United States Patent [19]

Colle et al.

[11] Patent Number: 5,081,141
[45] Date of Patent: Jan. 14, 1992

[54] FUNGICIDAL AZOLYL-DERIVATIVES

[75] Inventors: Roberto Colle, Basiglio; Francesco Corda, Milan; Giovanni Camaggi, Lodi; Franco Gozzo, S. Donato Milanese; Luigi Mirenna, Milan; Carlo Garavaglia, Cuggiono, all of Italy

[73] Assignee: Montedison S.p.A., Milan, Italy

[21] Appl. No.: 549,648

[22] Filed: Jul. 6, 1990

Related U.S. Application Data

[63] Continuation of Ser. No. 229,792, Aug. 4, 1988, abandoned, which is a continuation of Ser. No. 6,427, Jan. 23, 1987, abandoned.

[30] Foreign Application Priority Data

Jan. 23, 1986 [IT] Italy ............... 19169 A/86

[51] Int. Cl.$^5$ ............... A01N 43/653; C07D 249/08
[52] U.S. Cl. ............... 514/383; 548/262.2; 548/267.4; 548/267.8; 548/268.6
[58] Field of Search ............... 548/262.2, 267.4, 267.8, 548/268.6; 514/383

[56] References Cited

U.S. PATENT DOCUMENTS

| | | | |
|---|---|---|---|
| 4,338,327 | 7/1982 | Heeres et al. | 548/262 |
| 4,366,165 | 12/1982 | Miller et al. | 548/262 |
| 4,382,944 | 5/1983 | Kramer et al. | 514/383 |
| 4,507,140 | 3/1985 | Sugavanam | 548/262 |
| 4,518,604 | 5/1985 | Richardson et al. | 548/262 |
| 4,598,085 | 1/1986 | Heeres et al. | 548/262 |
| 4,690,942 | 9/1987 | Frick et al. | 548/341 |
| 4,895,865 | 1/1990 | Shaber et al. | 514/383 |

OTHER PUBLICATIONS

Mitsudera et al., "Synthesis and Fungicidal, etc.", Takeda Res. Lab. 41 pp. 145-153 (1982).

*Primary Examiner*—Patricia L. Morris
*Attorney, Agent, or Firm*—Stevens, Davis, Miller & Mosher

[57] ABSTRACT

Disclosed are compounds having the formula:

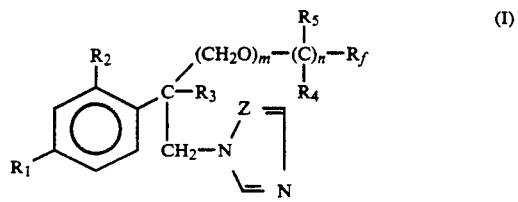

wherein:
m=0, 1;
n=0, 1;
Z=CH, N;
$R_1$ is selected from chlorine, bromine, fluorine, $CF_3$, phenyl, $C_1$-$C_2$-alkoxy, $C_1$-$C_2$-haloalkoxy, alkylthio, and haloalkylthio, wherein the halogen is Cl, Br, F;
$R_2$ is H, fluorine, chlorine, or bromine;
$R_3$ represents H, $CH_3$, CN, or also F when m=1 or when n=1 and $R_4$, $R_5$ are H;
$R_4$, $R_5$ are independently H or F;
$R_3$ and $R_4$, furthermore, when m=0, may represent, taken together, a second bond between the two carbon atoms to which they are linked in formula (I); and
$R_f$ is selected from the group consisting of polyfluoroalkyls, polyfluoroalkenyls and polyfluoroalkynyls containing up to 4 carbon atoms, containing at least 2 F atoms and, optionally, other halogens selected from Cl and Br.

Anti-fungal compositions containing these new compounds.

7 Claims, No Drawings

FUNGICIDAL AZOLYL-DERIVATIVES

This application is a continuation of application Ser. No. 229,792, filed Aug. 4, 1988, which in turn is a continuation of application Ser. No. 006,427, filed Jan. 23, 1987 both abandoned.

DESCRIPTION OF THE INVENTION

The present invention relates to azolyl-derivatives endowed with high fungicidal activity, to a process for their preparation, and to their related use in the agrarian field.

From U.K. Patent No. 1,589,852, 1-(2-aryl-2-R-ethyl)1H-1,2,4-triazoles having the following formula are known:

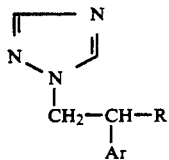

wherein R is alkyl, cycloalkyl, cycloalkylalkyl, alkenyl, arylalkyl, aryloxyalkyl. By the term "alkyl", the radical of an aliphatic hydrocarbon containing from 1 to 10 carbon atoms is meant.

We have found now a class of novel 1-(2-aryl-2-R-ethyl)-1H-azoles, wherein the radical R has meanings different from those of the prior art mentioned, and endowed with higher fungicidal activity.

An object of the present invention is therefore to provide a class of novel compounds having the formula:

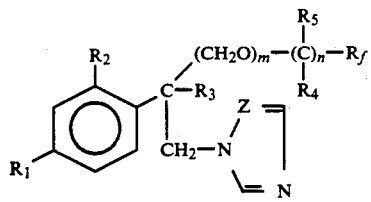

wherein:
m=0, 1;
n=0, 1;
Z=CH, N;
$R_1$ is selected from chlorine, bromine, fluorine, $CF_3$, phenyl, $C_1$–$C_2$-alkoxy, $C_1$–$C_2$-haloalkoxy, alkylthio, and haloalkylthio, wherein the halogen is Cl, Br, or F;
$R_2$ is H, fluorine, chlorine, or bromine;
$R_3$ represents H, $CH_3$, CN or also F when m=1 or when n=1 and
$R_4$, $R_5$ are H;
$R_4$, $R_5$ are independently H or F;
$R_3$ and $R_4$, when m=0, may furthermore represent, taken together, a second bond between the two carbon atoms to which they are linked in formula (I); and
$R_f$ is selected from the group consisting of polyfluoroalkyls, polyfluoroalkenyls and polyfluoroalkynyls containing up to 4 carbon atoms, and containing at least 2 F atoms and, optionally, other halogens selected from Cl and Br.

Examples of groups $R_f$ which may be introduced, according to the present invention, and which are indicated for nonlimitative purposes only are:
alkyls: —$CHF$—$CF_3$, —$CHBr$—$CF_3$, —$CHCl$—$CF_3$, —$CH_2$—$CF_3$, —$CF_2$—$CF_2H$, —$CF_2$—$CFH$—$CF_3$
alkenyls: —$CF$=$CF_2$, —$CF$=$CF$—$CF_3$, —$CH$=$CF$—$CF_3$, —$CH$=$CCl$—$CF_3$, —$CH$=$CBr$—$CF_3$, —$CH$=$C(CF_3)_2$;
alkynyls: —$C$≡$C$—$CF_3$.

The compounds according to the present invention may have one or more chiral center(s).

These compounds are generally obtained as racemic mixtures. These mixtures may be separated into the individual enantiomers by methods well known per se from the technical literature.

Both the individual enantiomers and the possible diastereoisomers or geometric isomers, generated by more chiral centers or by possible double bonds, are also objects of the present invention.

Objects of the present invention are also:
the salts of the compounds having formula (I) derived from an inorganic acid, such as a hydrogen halide, e.g., hydriodic, hydrobromic, hydrochloric acid; sulphuric, nitric, thiocyanic and phosphoric acid; or from an organic acid, such as acetic, propanoic, ethanedioic, propanedioic, benzoic, methanesulphonic, 4-methylbenzene-sulphonic, etc,;
the metal complexes obtained by the complexation reaction between the derivatives of formula (I) with an organic or inorganic salt of a metal, such as halide, nitrate, sulphate, phosphate of, e.g., copper, manganese, zinc or iron.

Examples of compounds of formula (I) according to the present invention are reported in Table 1.

TABLE 1

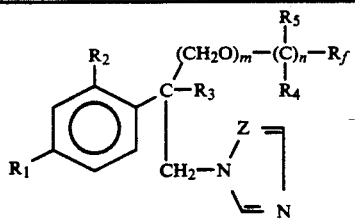

| Compound No. | $R_1$ | $R_2$ | $R_3$ | m | n | $R_4$ | $R_5$ | Z | $R_f$ | m.p. |
|---|---|---|---|---|---|---|---|---|---|---|
| 1 | Cl | H | H | 1 | 0 | — | — | N | —$CF_2$—$CF_2H$ | oil |
| 2 | Cl | Cl | H | 1 | 0 | — | — | N | —$CF_2$—$CF_2H$ | oil |
| 3 | Cl | Cl | H | 1 | 0 | — | — | N | —$CF_2$—$CFH$—$CF_3$ | oil |
| 4 | Cl | Cl | H | 1 | 0 | — | — | N | —$CF$=$CF$—$CF_3$ | oil |

The compounds having formula (I) may be obtained by employing different processes, according to the values taken by m and n and the nature of the group $R_3$. These different processes are briefly described below.

(1) A process for the preparation of compounds of formula (I) wherein m is 1 and n is 0, consists in adding an alcohol of formula

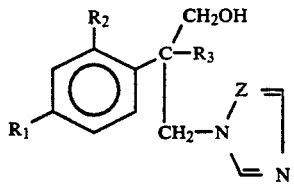 (II)

wherein $R_1$, $R_2$, $R_3$ and Z have the meanings specified above, to a 1,1-difluoroolefin having the formula:

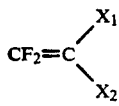

wherein $X_1$ is Cl, F, $CF_3$ and $X_2$ is F, $CF_3$, in an aprotic dipolar solvent, such as, e.g., dimethylformamide, or in an alcoholic solvent, such as e.g., tert.butanol, in the presence of either catalytic or stoichiometric amounts of a strong base, such as e.g., sodium hydride or potassium tert.butoxide, at temperatures within the range of from 20° to 100° C., to yield compounds having the formula:

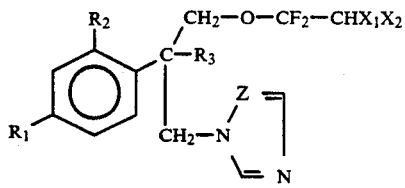 (Ia)

By a dehydrofluorination reaction, which may also take place spontaneously during the above-described reaction, a double bond may be introduced onto the carbon atom in the alpha-position of group $R_f$ of formula (I).

In turn, the intermediate alcohols of formula (II) may be prepared according to various methods.

(1a) A process for preparing the intermediate alcohols having the formula (II) wherein $R_3$ is H, $CH_3$, F, consists in reacting an ester of the formula:

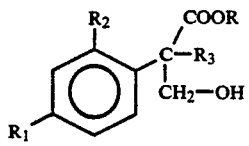 (V)

wherein R is either $CH_3$ or $C_2H_5$, known, or obtainable by known methods (Schwenker, Preuntzell, Gassner and Gerber, Chem. Ber., 99 (1966), 2407), with a halogenating agent such as, for example, $SOCl_2$, $POCl_3$, $PCl_5$, $PBr_3$, $PBr_5$, or a mesylating agent such as, e.g., methanesulphonyl chloride; or with a tosylating agent, such as, e.g., 4-methylphenylsulphonyl chloride, according to per se known procedures; in subsequently condensing the intermediate obtained, having formula:

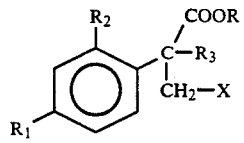 (IV)

wherein X represents a halogen, a mesyl radical or a tosyl radical, with the alkali-metal salt of an azole of formula

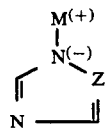

wherein M is an alkali metal and Z has the meaning given above, in an aprotic dipolar solvent, such as DMSO, DMF or acetone, at temperatures in the range of from 20° C. to the reflux temperatures of the solvent; and in finally subjecting the so-obtained intermediate compound having the formula:

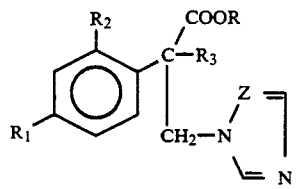 (III)

to reduction, by the use of such metal hydrides, as, e.g., LiAlH$_4$, in etheric solvents, such as ethyl ether or THF.

The intermediate esters of formula (III), wherein $R_3$ is H, may be prepared, according to an alternative route, by the addition of an azole of formula:

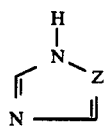

to a known compound of formula:

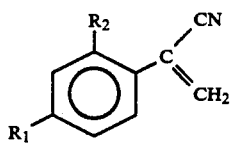 (IVb)

(known, for example, from Colonge, Dreux et Regeand, Bull. Soc. Chim. Fr., 1959, 1244), in apolar solvents such as, e.g., toluene or benzene, in the presence of catalytic amounts of an organic base such as, e.g., triethylamine, at boiling temperature, or in an alcoholic solvent, in the presence of either catalytic or stoichiometric amounts of an alkali-metal base, such as, e.g., NaOH or KOH, at the reflux temperature of the solvent, and in subsequently converting the —CN group of the intermediate obtained, of formula:

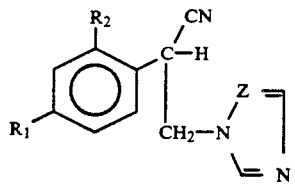

into a —COOR group, by treatment with mineral acids, such as, e.g., gaseous HCl, H$_2$SO$_4$, in alcoholic solvents, at temperatures within the range of from 0° C. to the boiling temperature of the solvent. By so operating, the esters (III) wherein R$_3$=H may be converted by reduction, as indicated above, into the alcohols (II), wherein R$_3$=H.

(1b) Another route for the preparation of the intermediate alcohols having formula (II) wherein R$_3$ is —CN consists in reacting the above intermediate of formula (IIIb) with paraformaldehyde or trioxymethylene, in aprotic dipolar solvent, such as e.g., DMSO or DMF, in the presence of catalytic amounts of a strong base such as e.g., sodium methoxide or sodium ethoxide, KOH, NaOH or sodium hydride, at temperatures between room temperature and 100° C.

(2) The compounds of formula (I), wherein m=1, n=1, R$_4$=R$_5$=H, may be obtained by the reaction of the alkali metal salt of a compound of formula (II), obtained by the reaction between a compound of formula (II) and a strong base such as, e.g., sodium hydride, with a fluorinated sulphonic ester having formula (VI), according to the following reaction scheme:

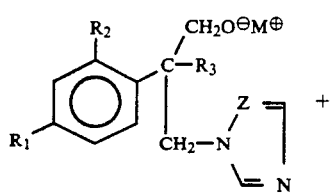

alkali-metal salt of (II)

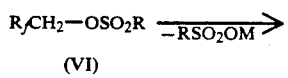

(VI)

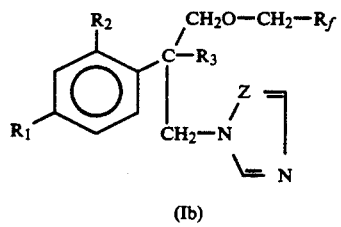

(Ib)

wherein R is CH$_3$, p-tolyl, CF$_3$.

The same compounds of formula (Ib) may also be obtained by the reaction of a sulphonic ester of compount (II) with the alkali-metal salt of the fluorinated alcohol R$_f$CH$_2$OH.

Examples of R$_f$ groups in compounds (VI) and in R$_f$CH$_2$OH alcohols are: —CF$_2$—CHF$_2$, —CF$_2$—CHFCF$_3$, —CF$_3$, —C$_2$F$_5$, —C$_3$F$_7$, —C$_4$F$_9$. From compounds having formula (Ib) wherein in the group R$_f$ at least a hydrogen atom is present, introducing a double bond into the same group may be done by a dehydrofluorination reaction.

(3) When m=0; n=0 or 1; and R$_3$=H, Me or F, the compounds having formula (I) may be prepared by starting from the carboxylic esters of formula (VII), as shown below, by reduction by methods per se known; for example, by using LiAlH$_4$, followed by the conversion of the alcoholic function so obtained into a leaving group (e.g., mesylate, tosylate, halogen) and finally by the condensation of the reactive intermediate resulting by such a conversion with an alkali-metal salt of the proper azole, by procedures analogous to those described for the preparation process (1. a) according to the reaction schemes:

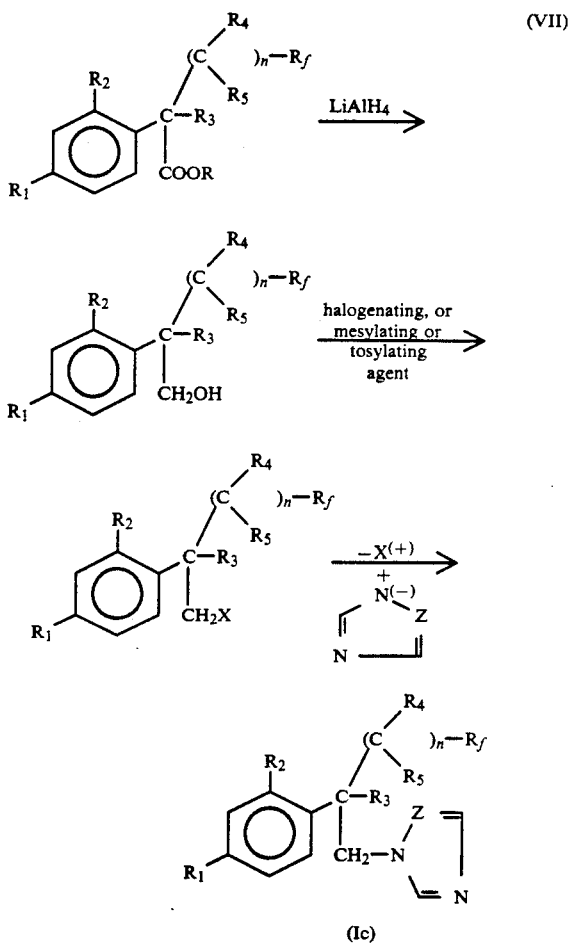

In the above formulae, R$_1$, R$_2$, R$_4$, R$_5$, R$_f$ and n have the meanings given above for the compound of formula (I); R$_3$ is H, CH$_3$ or F; and R is CH$_3$ or C$_2$H$_5$; X=halogen, mesyl, or tosyl.

The intermediate esters having formula (VII) may be prepared in their turn by various methods briefly described hereafter.

(3a) Condensation of the alkali-metal salt of an arylacetic ester of type (VIII), prepared according to known methods (e.g., from Middleton, Bingham, J.A.C.S. 1980, 102, 14, 4845-6), with a fluoroalkane

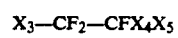

according to the reaction scheme:

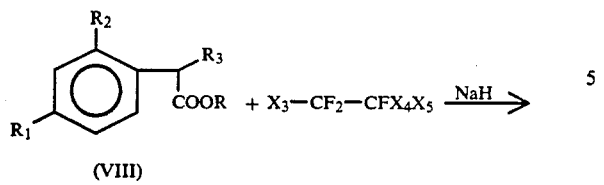 5

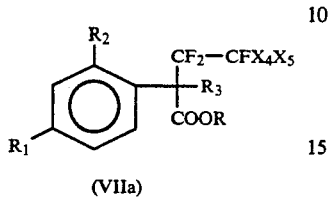

(VIIa)

wherein $R_3 = H$ or $CH_3$; $R = CH_3$ or $C_2H_5$; $X_3$ is bromine or iodine; $X_4$ is bromine or iodine; and $X_5$ may be fluorine or a $C_1-C_3$-per-fluoroalkyl.

The reaction may be carried out in a dipolar aprotic solvent such as DMF or DMSO, in an ether solvent, such as ethyl ether, THF or dioxane, at temperatures within the range of from room temperature to the reflux temperature of the solvent.

(3b) Dehydrofluorination of esters (VIIa) wherein $R_3 = H$, by strong bases in aprotic dipolar solvents, at temperatures within the range of from room temperature to the reflux temperature, or spontaneously during the same reaction for the preparation of compounds (VIIa), according to the scheme:

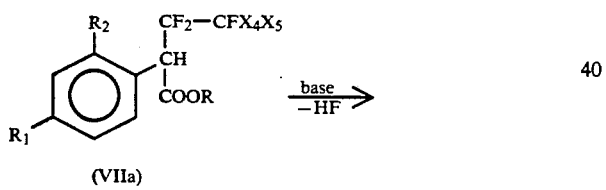

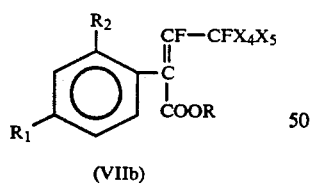

(VIIb)

(3c,d) By reduction of compounds (VIIa) or (VIIb) according to known methods, bu using, e.g., NaBH$_4$, Zn and acids, Na amalgam, hydrogen and catalysts, compounds of type:

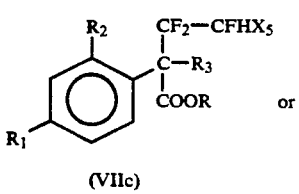

(VIIc)

-continued

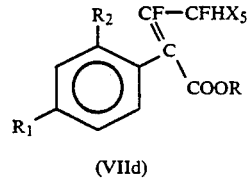

(VIId)

may be obtained.

From compounds of type (VIIc), wherein $R_3 = H$, introducing a double bond in the fluorinated chain may be done by a dehydrofluorination reaction.

(3e,f,g) Reduction of the compounds of formula:

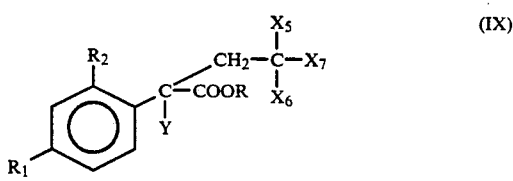

wherein $X_7$, $X_6$, equal to or different from each other, are F, Cl or Br; $X_5$ is either F or a $C_1-C_3$ perfluoroalkyl; Y is Br, I or also chlorine when $X_7$ and $X_6$ are F or Cl.

This reduction is carried out by methods known in the technical literature and, according to the selected experimental conditions and the reactant used, lead to compounds of formula:

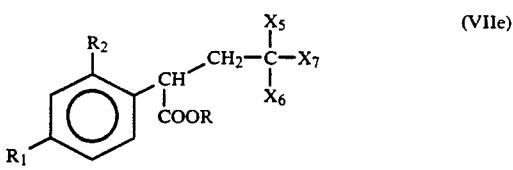

or of formula

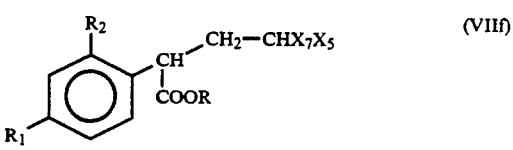

(when $X_6$ is $\neq F$), or of formula

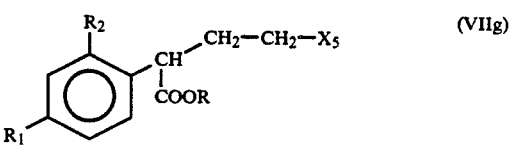

when $X_6$, $X_7$ are different from F.

(3h,i,l) By dehydrohalogenation by known procedures shown above, by starting from compounds of formula (IX), compounds of type

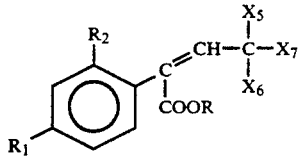
(VIIh)

may be obtained, from which, by reduction of the reactive halogens, one may arrive at compounds of type

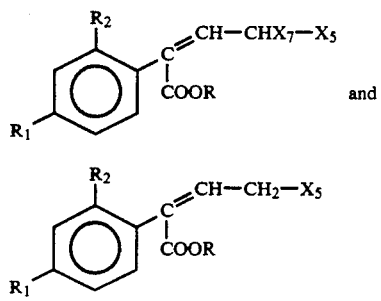

when $X_6$ and, respectively, $X_7$, are different from F.

Compounds of type (IX) of formula

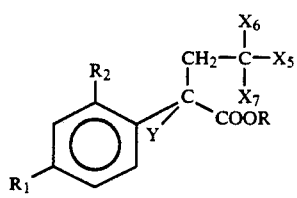
(IX)

are prepared in their turn by an addition reaction between the compounds known (e.g., from Schwenker, Preuntzell, Gassner and Gerber, Chem. Ber., 99 (1966), 2407), of formula:

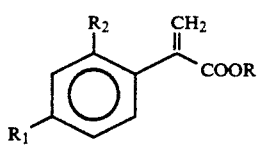
(X)

and a polyfluoroalkane of formula

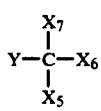

according to the reaction scheme:

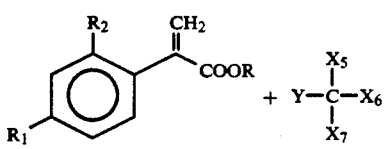
(IX)

The reaction is generally carried out in alcoholic solvents, such as tert.butanol, or in the absence of solvents, at temperatures within the range of from room temperature to 140° C., with known catalysts, such as benzoylperoxide or tert.butylperoxide, copper (I) chloride+ethanolamine or $FeCl_3$ or azobisisobutyronitrile and U.V. light.

(4) The compounds of formula (I) wherein m=0, n=0 and $R_3$=—CN may be prepared by the conversion of alcohols of formula (XI), through the reaction route analogous to that of process (3).

(XI)

(Id)

The intermediate alcohols of formula (XI) are prepared in their turn by starting from compounds for formula (XII) by the introduction of a methylol group, under conditions analogous to those illustrated above in the second reaction of process (1b):

(XII)

(XI)

Compounds (XII) can be prepared by starting from known benzyl nitriles of formula (XIII), by condensation with a fluoroalkane of formula $X_3$—$CF_2$—$CFX_4X_5$ under conditions analogous to those illustrated above in preparation (3a), according to the following scheme:

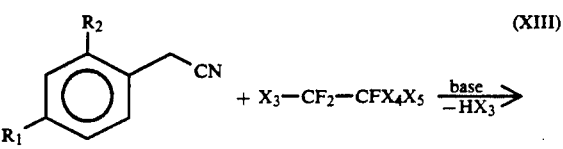
(XIII)

-continued

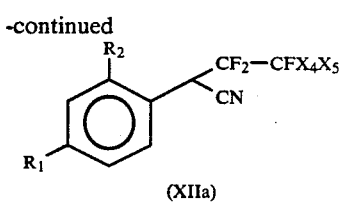

(XIIa)

From compounds (XIIa) one obtains, by a dehydrofluorination reaction, unsaturated compounds of formula:

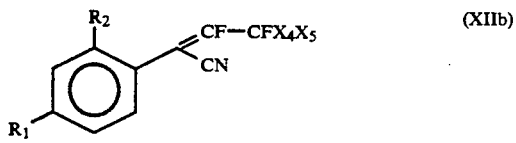

Finally, by starting from compounds XIIa and XIIb, by reduction according to methods per se known, one obtains compounds of formula

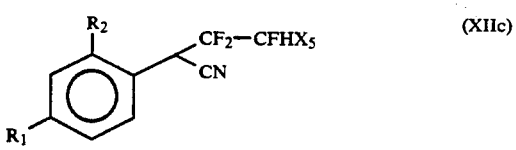

and respectively

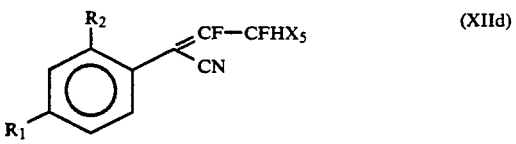

The compounds having formula (I) are endowed with a fungicidal activity that is particularly high against phytopathogenous fungi which attack cultivations of cereals, of Cucurbitaceae, of grapevine, and of fruit trees.

Examples of plant diseases which can be fought by the compounds of the present invention are the following:

Erysiphe graminis on cereals;
Sphaerotheca fuliginea of Cucurbitaceae (e.g., of cucumber)
Puccinia on cereals
Septoria on cereals
Helminthosporium on cereals
Rhyncosporium on cereals
Podosphaera leucotricha on apple-tree
Uncinula necator on grapevine
Venturia inaequalis on apple-tree
Piricularia oryzae on rice
Botrytis cinerea
Fusarium on cereals
and still further diseases.

The compounds having formula (I) are furthermore endowed with other positive and useful characteristics, such as fungicidal activity both curative and preventive in character, as well as a complete tolerability by the plants to be protected against the fungal infection.

Besides the high fungicidal activity with preventive and curative application, the compounds of formula (I) are also characterized by systemic properties.

These properties allow the products to enter into the vascular systems of plants, and act in sites (e.g., leaves) even very remote from those to which they are applied (e.g., roots).

For practical use in agriculture, having available fungicidal compositions containing one or more compounds of formula (I) as the active substance is often useful.

The application of these compositions may be carried out on any part of the plants, e.g., on leaves, stems, limbs and roots, or on the seeds of the plants before sowing, or also on the soil the plant is growing on.

Comositions may be used which have the form of dry powders, wettable pwders, emulsifiable concentrates, pastes, granulates, solutions, suspensions, and so forth: the selection of the particular type of composition will depend on the specific use.

The compositions are prepared in a per se known way, e.g., by diluting or dissolving the active substance with a solvent means and/or a solid diluent, optionally in the presence of surface-active agents. As solid diluents, or carriers, one may use: silica, kaolin, bentonite, talc, fossil flour, dolomite, calcium carbonate, magnesia, gypsum, clays, synthetic silicates, attapulgite, sepiolite. As liquid diluents, besides of course water, various types of solvents may be used such as, e.g., aromatic solvents (benzene, xylenes or mixtures of alkylbenzenes), chloroaromatic solvents (chlorobenzene), paraffins (petroleum fractions), alcohols (methanol, propanol, butanol), amines, amides (dimethylformamide), ketones (cyclohexanone, acetophenone, isophorone, ethyl-amyl-ketone), esters (isobutyl acetate). As surfactants: sodium, calcium or triethanolamine salts of alkylsulphates, alkylsulphonates, alkyl-arylsulphonates, polyethoxylated alkylphenols, fatty alcohols condensed with ethylene oxide, polyoxyethylated fatty acids, polyoxyethylated sorbitol esters, polyoxyethylated fats, lignine sulphonates may be used. The compositions may also contain special additives for particular purposes, e.g., such adhesive-properties-conferring agents as gum arabic, polyvinyl alcohol, polyvinylpyrrolidone, etc.

If desired, to the compositions of the present invention also other compatible active substances such as fungicides, phytomedicines, phytoregulators, herbicides, insecticides, fertilizers, etc., may be added.

The concentration of active substance in the said compositions may vary over a wide range, according to the active compound, the cultivation, the pathogenic agent, the environmental conditions, and the type of formulation adopted. In general, the concentration of active substance will vary from 0.1 to 95%, and preferably from 0.5 to 90% by weight.

The following examples are given in order still better to illustrate the invention.

EXAMPLE 1

Preparation of 1-(1H-1,2,4-triazol-1-yl)-2-(4-chlorophenyl)-3-(1,1,2,2-tetrafluoroethoxy)-propane (Compound No. 1).

An amount of 0.4 g of NaH in oil suspension at 55% is dispersed in 10 ml of anhydrous DMF under nitrogen atmosphere. At room temperature, 2.4 g of 2-(4-chlorophenyl)-3-(1H-1,2,4-triazol-1-yl)-propanol dissolved in 10 ml of anhydrous DMF is added. When the reaction is complete (over a time of about 30 minutes), the reaction mixture is cooled to 0° C., and tetrafluoroethylene is added, the flow rate thereof being so adjusted that the reaction temperature does not exceed 30° C.

At the end of heat evolution, the temperature is allowed to rise again to room temperature.

The reaction mixture is poured into water, and is extracted with dichloromethane. The organic extract is washed with water, dried over Na$_2$SO$_4$ and evaporated under vacuum. The residual oil (2.9 g) is purified over silica gel, using 8:2 n-hexane+diethylether as the eluent. 0.5 g of a colorless viscous oil is obtained, which is characterized as having the structure indicated in the title of this example on the basis of the following spectroscopic data:

I.R. ($\nu$, cm$^{-1}$): 680, 1120, 1210, 1275, 1500.

$^1$H-N.M.R. (200 MHz) in CDCl$_3$, $\delta$=3.56 quint., 1H) 4.11 (m, 2H) 4.42 (2 dd, 2H) 5.667 (tt, 1H) 6.945–7.013; 7.181–7.249 (2 m, 4H) 7.681 (s, 1H) 7.853 (s, 1H).

EXAMPLE 2

Preparation of 2-(4-chlorophenyl)-3-(1H-1,2,4-triazol-1-yl)-propanol 1.3 g of LiAlH$_4$ is suspended in 170 ml of anhydrous diethyl ether under N$_2$ atmosphere. Within one hour, 8 g of methyl α-(1H-1,2,4-triazol-1-ylmethyl)-4-chlorophenylacetate is introduced. The reaction is exothermic, and proceeds with solvent reflux. At the end of heat evolution, 10 ml of methanol in 50 ml of diethyl ether is added to destroy the excess of hydride.

The reaction mixture is filtered over celite and from the filtrate, after concentration, 6.8 g of a solid product is obtained which is washed with a few ml of n-hexane-acetone mixture, to obtain 5.3 g of a white solid (m.p. 137°–9° C.) having the structure indicated in the title of this example.

I.R. ($\nu$, cm$^{-1}$) in oil: 830, 1018, 1065, 1140, 1284, 3115, 3210.

EXAMPLE 3

Preparation of methyl α-(1H-1,2,4-triazol-1-yl)-4-chlorophenylacetate

A suspension of 3.2 g of 1,2,4-triazole and 8.3 g of K$_2$CO$_3$ in 300 ml of anhydrous acetone is refluxed over 1 hour. After cooling to 10° C., 14 g of methyl α-(methanesulphonyloxymethyl-4-chlorophenyl-acetate is added. The temperature is then allowed to spontaneously rise to room temperature, and the reaction mixture is stirred for one hour, is filtered over fritted glass and the filtrate is concentrated under vacuum, 13 g thus being obtained of raw solid product, which is suspended with 10 ml of 1:1 n-hexane+ethanol mixture.

10.8 g is thus obtained of a white solid (m.p. 92°–3° C.), having the structure indicated in the title of this example.

I.R. ($\nu$, cm$^{-1}$) in oil: 840, 1019, 1092, 1142, 1225, 1743.

EXAMPLE 4

Preparation of methyl α-(methanesulphonyloxymethyl)-4-chlorophenyl-acetate

To a solution of 5 g of methyl α-(hydroxymethyl)-4-chlorophenylacetate and 3.5 g of methanesulphonyl chloride in 30 ml of anhydrous diethyl ether, cooled at 0° C., a solution of 2.6 g of triethylamine in 10 ml of anhydrous diethyl ether is added dropwise. The temperature is allowed to rise again to room temperature, the reaction mixture is poured into water and is extracted with diethyl ether. The ether solution, washed with water, and dried over Na$_2$SO$_4$, is concentrated under vacuum, to yield 7.2 g of raw product. By crystallization thereof from 5 ml of ethanol, 5.4 g of a white solid product (m.p. 77°–8° C.) is obtained, having the structure indicated in the title of this example.

I.R. ($\nu$, cm$^{-1}$): 1100, 1180, 1210, 1492, 1725.

EXAMPLE 5

Preparation of 1-(1H-1,2,4-triazol-1-yl)-2-(2,4-dichlorophenyl)-3-(1,1,2,2,-tetrafluoroethoxy)-propane (Compound No. 2)

This compound is prepared by a process similar to that disclosed in Example 1, by starting from 2-(2,4-dichlorophenyl)-3-(1H-1,2,4-triazol-1-yl)-propanol, prepared in its turn by a process similar to that described in Examples 4, 3 and 2.

Compound No. 2 is isolated as a colorless viscous oil and is characterized by the following spectroscopic data:

I.R. ($\nu$, cm$^{-1}$): 683, 1120, 1210, 1278, 1478, 1505.

$^1$H-N.M.R. (60 MHz) in CCl$_4$, $\delta$=4–4.7 (m, 5H) 5.72 (tt, 1H) 7–7.6 (m, 3H) 7.74 (s, 1H) 7.8 (s, 1H).

EXAMPLE 6

Preparation of methyl 2-(4-chlorophenyl)-4-bromo-3,4,5,5,5-pentafluoropent-2-enoate 0.8 g of sodium hydride in oil suspension at 55% is dispersed in 10 ml of anhydrous DMF under N$_2$ atmosphere.

At room temperature, 3 g of methyl 4-chlorophenylacetate dissolved in 10 ml of anhydrous DMF is added. When the reaction is complete (over a time of about 30 minutes), the reaction mixture is added dropwise, under N$_2$ atmosphere, to a solution of 5 g of 1,2-dibromo-1,1,2,3,3,3-hexafluoropropane in 10 ml of anhydrous DMF. After 1 hour at room temperature, the reaction mixture is poured into water, and is extracted with dichloromethane. The organic extract is washed with water up to neutral pH, dried over Na$_2$SO$_4$ and evaporated under vacuum to yield 4 g of raw product. This is pruified by chromatography over silica gel, using 95:5 n-hexane+diethylether as the eluent. 1.5 g of a slightly yellow liquid is obtained, having the structure indicated in the title to this example, according to the following spectroscopic data:

I.R. ($\nu$, cm$^{-1}$): 900, 1125, 1220, 1282, 1492, 1594, 1664, 1740.

$^1$H-N.M.R. (60 MHz) in CCl$_4$, $\delta$=3.82 (s, 3H) 7.43 (s broad, 4H).

EXAMPLE 7

Preparation of 1-(1H-1,2,4-triazol-1-yl)-2-(2,4-dichlorophenyl)-3-(1,1,2,3,3,3-hexafluoropropyloxy)-propane (Compound No. 3) and of 1-(1H-1,2,4-triazol-1-yl-2-(2,4-dichlorophenyl)-3-(1,1,2,3,3,3-hexafluoropropeneoxy)-propane (Compound No. 4)

The above-mentioned compounds were obtained as a mixture, by starting from 2-(2,4-dichlorophenyl)-3-(1H-1,2,4-triazol-1-yl)propanol and hexafluoropropene, and by a process analogous to that described in Example 1.

The compounds were isolated as colorless viscous oils, and characterized by the following spectroscopic date:

Compound No. 3

I.R. ($\nu$, cm$^{-1}$): 1760, 1590, 1510, 1478, 1280, 1190, 1040.

$^1$H-N.M.R. (60 MHz) in CCl$_4$, $\delta$=7.75 (s, 1H) 7.7 (s, 1H) 7.5–6.8 (m, 3H) 5.25 (m, 0.5H) 4.4–4.45 (d, 2H) 4.2 (s broad, 2H) 4.7–3.8 (m, 1.5H).

Compound No. 4

The I.R. spectrum is the same as that of Compound No. 3, with the exception of the band at 1760 cm$^{-1}$, which is absent.

$^1$H-N.M.R. (60 MHz) in CCl$_4$, $\delta$=7.75 (s, 1H) 7.7 (s, 1H) 7.5–6.8 (m, 3H) 4.4–4.45 (d, 2H) 4.2 (s broad, 2H) 4.55–3.8 (m, 1H).

EXAMPLE 8

Preparation of 1-(1,2,4-triazol-1-yl)-2-(4-chlorophenyl)-2-(1,1,2,2-tetrafluoroethoxy)-methyl-propane (Compound No. 5)

An amount of 6.1 of potassium tert-butoxide is added, under nitrogen atmosphere at $-10°$ C., to 1.9 g of 2-(4-chlorophenyl)-2-methyl-3-(1,2,4-triazol-1-yl)-1-hydroxy-propane dissolved in 6.5 ml of anhydrous THF, 13 ml. of anhydrous DMSO, and 13 ml of anhydrous tert. butanol. The apparatus is then first put under vacuum and tetrafluoroethylene is introduced by maintaining the reaction mass under this gas atmosphere over a time of one night, at room temperature. The reaction mixture then is poured into water, and extracted with ethyl acetate. The extract is washed with water, dried over Na$_2$SO$_4$ and evaporated; the raw product obtained is purified by chromatography over silica gel, using n-hexane-ethyl acetate 1:1 as eluent. 1 g of an oil is isolated having the structure indicated in the title of this example, according to the following spectroscopic data:

I.R. (cm$^{-1}$) 1580, 1280, 1210, 1120.

NMR$^{1H}$(60 MHz) TMS in CDCl$_3$, $\delta$=1.30 (s, 3H) 4.0 (s broad, 2H) 4.25 (s broad, 2H) 5.55 (tt, 1H) 6.8–7.2 (m, 4H) 7.35 (s, 1H) 7.55 (s, 1H).

Similarly to compound No. 5, 1-(1,2,4-triazol-1-yl)-2-(2,4-dichlorophenyl)-2-(1,1,2,2-tetrafluoroethoxymethylpropane is prepared. The compound is characterized by the following spectroscopic data:

N.M.R. $^1$H (60 MHz) TMS in CDCl$_3$, $\delta$=1.35 (s, 3H) 3.9 (s broad, 2H) 4.05 (s broad, 2H) 5.5 (tt, 1H) 6.8–7.2 (m, 3H) 7.45 (s, 1H) 7.6 (s, 1H).

EXAMPLE 9

Determination of the Fungicidal Activity against Cucumber Oidium (*Sphaerotheca fuliginea* (Sclech) Salmon)

Preventive activity

Cucumber plants, cv. Marketer, grown in pot in a conditioned environment, were sprinkled on the lower faces of their leaves with the product under test in a water-acetonic solution at 20% (v/v) of acetone. The plants were subsequently kept in a conditioned environment for 1 day, and were then sprinkled on the upper face of their leaves with an aqueous suspension of conidia of *Sphaerotheca fuliginea* (200,000 conidia per ml). The plants were then placed again in a conditioned environment.

At the end of the incubation time of the fungus (8 days), the severity of the infection was visually evaluated, and given a rating based on an evaluation scale from 100 (=healthy plant) to 0 (=completely infected plant).

The results are reported in Table 2.

Curative Activity

Plants of cucumber cv. Marketer, grown in pot in a conditioned environment, were sprayed on the upper face of the leaves with an aqueous solution of conidia of *Sphaerotheca fuliginea* (200,000 conidia per ml). After 24 hours from the time of infection, the plants were treated with the products under test in a water-acetonic solution at 20% (v/v of acetone), by spraying same on both faces of their leaves.

At the end of the incubation time of the fungus (8 days), during which the plants were stored in a suitably conditioned environment, the severity of the infection was visually evaluated, and given a rating based on an evaluation scale from 100 (=healthy plant) to 0 (=completely infected plant).

The results are reported in Table 2.

EXAMPLE 10

Determination of the Fungicidal Activity against the Oidium of Wheat (*Erysiphe graminis* D.C.)

Preventive activity

The leaves of wheat, cv. Irnerio, grown in pot in a conditioned environment, were treated by sprinkling both their faces with the products under test in a water-acetonic solution at 20% (v/v) of acetone.

After one day of storage in a conditioned environment, the plants were sprinkled on both faces of their leaves with an aqueous suspension of *Erysiphe graminis* (200,000 conidia per ml). After 24 hours of storage in a humidity-saturated environment, at 21° C., the plants were kept in a conditioned environment for incubation of the fungus.

At the end of said incubation period (12 days), the severity of the infection was evaluated visually, and given a rating based on an evaluation scale from 100 (=healthy plant) to 0 (=completely infected plant).

The results are reported in Table 2.

Curative activity

The leaves of wheat, cv. Irnerio, grown in pot in a conditioned environment, were sprayed on both their faces with an aqueous suspension of *Erysiphe graminis* (200,000 conidia per ml). After 24 hours of storage in a humidity-saturated environment, at 21° C., the leaves were treated with the products under test in a water-acetonic solution at 20% (v/v of acetone), by spraying same on both their faces.

At the end of the incubation time (12 days), the severity of the infection was visually evaluated, and was given a rating based on an evaluation scale from 100 (=healthy plant) to 0 (=completely infected plant).

The results are reported in Table 2.

EXAMPLE 11

Determination of the Fungicidal Activity against the Linear Blight of Wheat (*Puccinia graminis* Pers.)

Preventive activity

The leaves of wheat, cv. Irnerio, grown in pot in a conditioned environment, were treated by sprinkling both their faces with the products under test in a water-acetonic solution at 20% (v/v) of acetone. After one day of storage in an environment conditioned at 23° C. and 70% R.H., the plants were sprinkeld on both faces of their leaves with a mixture of spores of *Puccinia graminis* in talc (100 mg of spores per 5 g of talc). After 48 hours of storage in a humidity-saturated environment, at 21° C., the plants were kept in a conditioned environment for the incubation of the fungus.

At the end of said incubation period (14 days), the severity of the infection was evaluated visually, and given a rating based on an evaluation scale form 100 (=healthy plant) to 0 (=completely infected plant).

The results are reported in Table 2.

Curative activity

The leaves of wheat, cv. Irnerio, grown in pot in a conditioned environment, were sprayed on both faces with a mixture of spores of *Puccinia graminis* in talc (100 mg of spores/5 g of talc); after 48 hours of storage in a humidity-saturated environment, at 21° C., the leaves were treated with the products under test in a water-acetonic solution at 20% (v/v of acetone), by spraying both their faces.

At the end of the incubation time (14 days), the severity of the infection was visually evaluated, and given a rating based on an evaluation scale from 100 (=healthy plant) to 0 (=completely infected plant).

The results are reported in Table 2.

TABLE 2

| Compound No. | Dose g/l | *Sphaerotheca fuliginea*/cucumber | | *Erysiphe graminis* trit./wheat | | *Puccinia graminis*/ Wheat | |
|---|---|---|---|---|---|---|---|
| | | Preventive Activity | Curative Activity | Preventive Activity | Curative Activity | Preventive Activity | Curative Activity |
| 1 | 0.5 | 100 | 100 | 100 | 100 | 100 | 100 |
| | 0.25 | 100 | 100 | 100 | 100 | 100 | 100 |
| | 0.125 | 100 | 100 | 100 | 100 | 70 | 100 |
| 2 | 0.5 | 100 | 100 | 100 | 100 | 100 | 100 |
| | 0.25 | 100 | 100 | 100 | 100 | 100 | 100 |
| | 0.125 | 100 | 100 | 100 | 100 | 100 | 100 |
| Ref.* | 0.5 | 100 | | 100 | | 50 | |
| | 0.25 | 100 | | 100 | | 0 | |
| | 0.125 | 100 | | 100 | | 0 | |

Ref* corresponds to the reference compound 1-[2-(2,4-dichlorophenyl)pentyl]-1H-1,2,4-triazole, known as Penconazole (Topas), of U.K. Pat. No. 1,589,852.

EXAMPLE 12

Determination of the Foliar Systemic Activity on Wheat Oidium (*Erysiphe graminis* d.c.)

The leaves of wheat, cv. Irnerio, grown in pot in a conditioned environment, were treated by sprinkling both their faces with the products under test in a water-acetonic solution at 20% (v/v) of acetone. Five days after the treatment, the leaves treated, and the new leaves emitted in the meantime, were sprinkled on both faces with an aqueous suspension of *Erysiphe graminis* (200,000 conidia per cc). After 24 hours of storage in a humidity-saturated environment, at 21° C., the plants were kept in a conditioned environment for the incubation of the fungus.

At the end of said incubation period (12 days), the severity of the infection was evaluated visually, and given a rating based on an evaluation scale from 100 (=healthy plant) to 0 (=completely infected plant).

The results shown in Table 3 were obtained.

TABLE 3

| | Foliar Systemic Activity on *Erysiphe graminis* | | |
|---|---|---|---|
| Compound No. | Treated Dose, g/l | Treated Leaves | Untreated Leaves |
| 2 | 0.0018 | 100 | 100 |
| Penconazole | 0.0018 | 42 | 14 |
| Propiconazole | 0.0018 | 40 | 30 |

TABLE 3-continued

| | Foliar Systemic Activity on *Erysiphe graminis* | | |
|---|---|---|---|
| Compound No. | Treated Dose, g/l | Treated Leaves | Untreated Leaves |
| Triadimefon | 0.0018 | 0 | 0 |

Propiconazole = 1-[2-(2,4-dichlorophenyl)-4-propyl-1,3-dioxolan-2-yl-methyl]-1H-1,2,4-triazole.
Triadimefon = 1-(4-chlorophenoxy)-3,3-dimethyl-1-(1H-1,2,4-triazol-1-yl)-butanone.

EXAMPLE 13

Determination of the Foliar Systemic Activity on Linear Blight of Wheat (*Puccinia graminis* Pers.)

The leaves of wheat, cv. Irnerio, grown in pot in a conditioned environment, were treated by sprinkling both their faces with the products under test in a water-acetonic solution at 20% (v/v) of acetone. Five days after treatment, the leaves treated, and the new leaves emitted in the meantime, were sprinkled on both faces with a mixture of spores of *Puccinia graminis* in talc (100 mg of spores/5 g of talc). After 48 hours of storage in a humidity-saturated environment, at 21° C., the plants were kept in a conditioned environment for the incubation of the fungus.

At the end of said incubation period (14 days), the severity of the infection was evaluated visually, and given a rating based on an evaluation scale ranging from 100 (=healthy plant) to 0 (=completed infected plant).

The results shown in Table 4 were obtained.

TABLE 4

| | Foliar Systemic Activity on *Puccinia graminis* Pers. | | |
|---|---|---|---|
| Compound No. | Treated Dose, g/l | Treated Leaves | Untreated Leaves |
| 2 | 0.5 | 100 | 100 |
| Penconazole | 0.5 | 20 | 0 |

EXAMPLE 14

Determination of the fungicidal activity on brown-spotting of apple-tree (*Venturia inaequalis* (cke) Wint)

Preventive activity

The leaves of apple-tree, cv. Starking, grown in pot in a greenhouse, were treated by sprinkling both faces with the products under test in a water-acetonic solution at 20% (v/v) of acetone. After one day of storage in an environment conditioned at 20° C. and 70% R.H., the plants were sprinkled on both faces of their leaves with an aqueous suspension of conidia of *Venturia inaegualis* (200,000 conidia per cc). After 2 days of storage in a humidity-saturated environment, at 21° C., the plants were stored in a conditioned environment for the incubation of the fungus.

At the end of said incubation period (14 days), the severity of the infection was evaluated visually, and given a rating based on an evaluation scale ranging from 100 (=healthy plant) to 0 (=completely infected plant).

The results are reported in Table 5.

Curative activity

The leaves of apple-tree, cv. Starking, grown in pot in a greenhouse, were uniformly sprinkled with an aqueous suspension of conidia of *Venturia inaequalis* 200,000 conidia per cc). After 2 days of storage in a humidity-saturated environment, said leaves were treated with the products being tested in a water-acetonic solution at 20% (v/v) of acetone, by sprinkling both their faces.

At the end of the incubation time (14 days), the severity of the infection was evaluated visually, and given a rating based on an evaluation scale from 100 (=healthy plant) to 0 (=completely infected plant).

The results are reported in Table 5.

TABLE 5

| Activity on *Venturia inaequalis* (Cke) Wint. | | | |
|---|---|---|---|
| Compound No. | Dose, g/l | Preventive Activity | Curative Activity |
| 2 | 0.05 | 100 | 100 |
| Penconazole | 0.05 | 88 | 88 |
| Propiconazole | 0.05 | 77 | 75 |

What is claimed is:

1. A compound of the formula

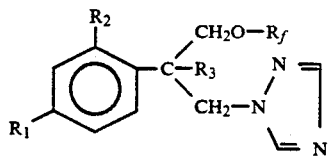

wherein $R_1$ is selected from the group consisting of chlorine, bromine, fluorine, $-CF_3$, phenyl, $C_1-C_2$-alkoxy and $C_1-C_2$ haloalkoxy, wherein the haloalkoxy is a Cl, Br or F haloalkoxy;

$R_2$ is selected from the group consisting of H, fluorine, chlorine and bromine;

$R_3$ is selected from the group consisting of a hydrogen atom and $CH_3$; and $R_f$ is selected from the group consisting of polyfluoroalkyls, polyfluoroalkenyls and polyfluoroalkynyls containing up to 4 carbon atoms, and containing at least two fluorine atoms.

2. A compound according to claim 1, characterized in that $R_f$ represents an alkyl containing up to 4 carbon atoms, and at least 2 fluorine atoms.

3. A compound according to claim 1, which is 1-(1H-1,2,4-triazol-1-yl)-2-(2,4-dichlorophenyl)-3-(1,1,2,2-tetrafluoroethoxy)-propane.

4. A method for fighting fungal infestations in useful plants consisting in distributing on the plant, on the seeds thereof, or on the surrounding ground, when the fungal infestation is expected or is already in progress, an efficacious amount of a compound as defined in claim 1, as such or in the form of a suitable composition.

5. A method for fighting fungal infestations in useful plants consisting in distributing on the plant, on the seeds or on the surrounding ground, when the fungal infestation is expected or is already in progress, an efficacious amount of the compound 1-(1H-1,2,4-triazol-1-yl)-2-(2,4-dichlorophenyl)-3-(1,1,2,2-tetrafluoroethoxy)-propane as defined in claim 3, either as such, or in the form of a suitable composition.

6. Antifungal composition containing as the active ingredient an effective amount of one or more compounds as defined in claim 1, together with an agriculturally-acceptable solid or liquid carrier.

7. Antifungal composition containing as the active ingredient an effective amount of the compound as defined in claim 3, together with an agriculturally-acceptable solid or liquid carrier.

* * * * *